United States Patent
Wallace

(10) Patent No.: US 7,309,345 B2
(45) Date of Patent: Dec. 18, 2007

(54) METHOD AND SYSTEM FOR DELIVERING AN IMPLANT UTILIZING A LUMEN REDUCING MEMBER

(75) Inventor: Michael P. Wallace, Fremont, CA (US)

(73) Assignee: Boston Scientific-Scimed, Inc., Maple Grove, MN (US)

( * ) Notice: Subject to any disclaimer, the term of this patent is extended or adjusted under 35 U.S.C. 154(b) by 634 days.

(21) Appl. No.: 10/627,024

(22) Filed: Jul. 25, 2003

(65) Prior Publication Data
US 2005/0021072 A1    Jan. 27, 2005

(51) Int. Cl.
*A61M 31/00* (2006.01)
(52) U.S. Cl. .................. 606/191; 128/898; 623/1.11
(58) Field of Classification Search ................ 128/898; 606/190–198; 623/1–12
See application file for complete search history.

(56) References Cited

U.S. PATENT DOCUMENTS

| | | | |
|---|---|---|---|
| 5,370,660 A | | 12/1994 | Weinstein et al. |
| 5,795,331 A | | 8/1998 | Cragg et al. |
| 5,814,062 A | * | 9/1998 | Sepetka et al. ............ 606/198 |
| 5,893,868 A | * | 4/1999 | Hanson et al. ............ 623/1.11 |
| 5,916,235 A | | 6/1999 | Guglielmi |
| 5,928,260 A | | 7/1999 | Chin et al. |
| 5,951,599 A | | 9/1999 | McCrory |
| 5,968,069 A | * | 10/1999 | Dusbabek et al. .......... 606/194 |
| 6,007,543 A | * | 12/1999 | Ellis et al. ................... 606/108 |
| 6,036,723 A | * | 3/2000 | Anidjar et al. ............. 623/1.13 |
| 6,074,407 A | | 6/2000 | Levine et al. |
| 6,077,260 A | * | 6/2000 | Wheelock et al. ............ 606/32 |
| 6,093,199 A | | 7/2000 | Brown et al. |
| 6,132,450 A | * | 10/2000 | Hanson et al. .............. 606/198 |

(Continued)

FOREIGN PATENT DOCUMENTS

WO    WO 01/56501    8/2001

OTHER PUBLICATIONS

PCT International Search Report for PCT/US2004/016966, Applicant: Scimed Life Systems, Inc., Forms PCT/ISA/210 and 220, dated Dec. 2, 2004 (9 pages).

(Continued)

*Primary Examiner*—Henry M Johnson, III
(74) *Attorney, Agent, or Firm*—Vista IP Law Group, LLP

(57) ABSTRACT

A method and system for inserting an implant, such as vaso-occlusive device, an embolic containment device, or a stent into a vascular space to a vascular site in a body utilizing a lumen-reducing catheter. The method and system can be used to treat aneurysm, tumors and other vascular malformations. A guide is inserted into the vascular space. First and second catheters are inserted into the vascular space along the guide. The first or delivery catheter defines a first cavity, and the second or lumen-reducing catheter defines a second, smaller cavity. The second catheter is inserted within the first catheter. In one embodiment, an implant is advanced together with the first and second catheters to a vascular site. In an alternative embodiment, after the first and second catheters are positioned, the guide and the second catheter are removed from the first cavity, and an implant is inserted through the first cavity. With these configurations, radial movement of the guide is restricted to the smaller, second cavity rather than the larger, first cavity.

21 Claims, 7 Drawing Sheets

U.S. PATENT DOCUMENTS

| | | | |
|---|---|---|---|
| 6,152,944 A * | 11/2000 | Holman et al. | 623/1.11 |
| 6,238,415 B1 * | 5/2001 | Sepetka et al. | 606/213 |
| 6,315,790 B1 * | 11/2001 | Gerberding et al. | 623/1.11 |
| 6,344,041 B1 | 2/2002 | Kupiecki et al. | |
| 6,344,048 B1 | 2/2002 | Chin et al. | |
| 6,375,668 B1 | 4/2002 | Gifford et al. | |
| 6,416,529 B1 * | 7/2002 | Holman et al. | 606/194 |
| 6,440,097 B1 | 8/2002 | Kupiecki | |
| 6,527,790 B2 | 3/2003 | Chien et al. | |
| 6,613,074 B1 | 9/2003 | Mitelberg et al. | |
| 6,663,607 B2 * | 12/2003 | Slaikeu et al. | 604/265 |
| 6,663,660 B2 * | 12/2003 | Dusbabek et al. | 623/1.11 |
| 6,849,081 B2 * | 2/2005 | Sepetka et al. | 606/213 |
| 6,991,639 B2 * | 1/2006 | Holman et al. | 606/194 |
| 2001/0002438 A1 * | 5/2001 | Sepetka et al. | 606/198 |
| 2001/0029362 A1 | 10/2001 | Sirhan et al. | |
| 2002/0013599 A1 | 1/2002 | Limon et al. | |
| 2002/0072763 A1 | 6/2002 | Chien et al. | |
| 2002/0095203 A1 | 7/2002 | Thompson et al. | |
| 2002/0120297 A1 * | 8/2002 | Shadduck | 607/2 |
| 2002/0151953 A1 | 10/2002 | Chobotov et al. | |
| 2002/0169473 A1 | 11/2002 | Sepetka et al. | |
| 2003/0004461 A1 | 1/2003 | Kupiecki | |
| 2003/0093106 A1 | 5/2003 | Brady et al. | |
| 2003/0163192 A1 * | 8/2003 | Wallace et al. | 623/1.11 |
| 2003/0204168 A1 * | 10/2003 | Bosma et al. | 604/103.02 |
| 2003/0204246 A1 * | 10/2003 | Chu et al. | 623/1.23 |

OTHER PUBLICATIONS

PCT Written Opinion of the International Search Authority for PCT/US2004/016966, Applicant: Scimed Life Systems, Inc., Form PCT/ISA/237, dated Dec. 2, 2004 (7 pages).

* cited by examiner

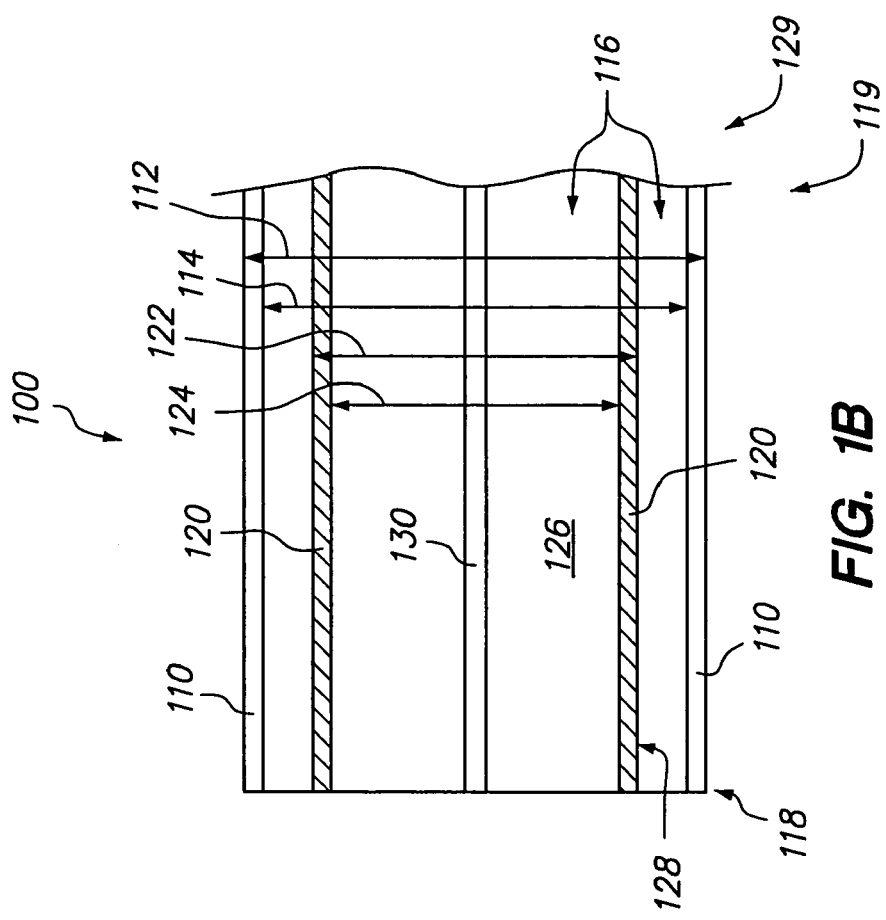
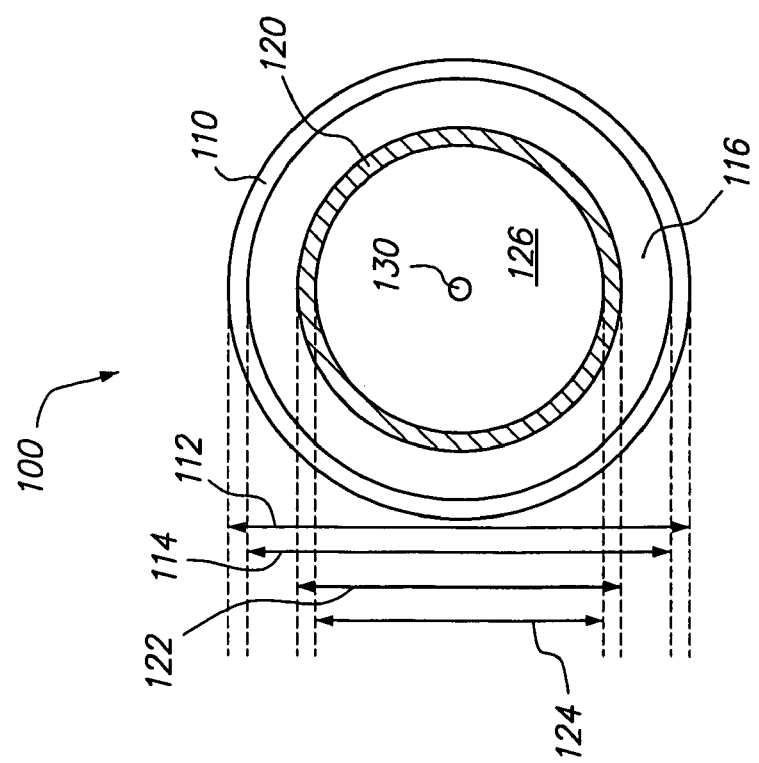

METHOD AND SYSTEM FOR DELIVERING AN IMPLANT UTILIZING A LUMEN REDUCING MEMBER

FIELD OF THE INVENTION

The field of the invention relates to implantable devices, and more particularly, to a method and system for inserting a delivery sheath or catheter through a vascular body using a lumen-reducing catheter and delivering an implantable device through the delivery catheter or the lumen-reducing catheter.

BACKGROUND

In many clinical situations, blood vessels are occluded with various implants to control bleeding, prevent blood supply to tumors, block blood flow within an aneurysm or other vascular malformations. Intracranial aneurysms, for example, may rupture causing significant bleeding. The significant bleeding may permanently damage the surrounding brain tissue, possibly causing serious injury and death. Intracranial aneurysms may be particularly difficult to access and treat when they are formed in remote cerebral blood vessels. If left untreated, hemodynamic forces of normal pulsatile blood flow can rupture fragile tissue in the area of the aneurysm causing a stroke.

Various implants have been used to occlude vascular sites. For example, vaso-occlusive devices are surgical implants that are delivered through a catheter in a blood vessel or vascular cavity and placed within aneurysm to form a thrombus and occlude the aneurysm. In one conventional system, a guide wire is inserted through a vascular cavity. An outer catheter or sheath is guided by the wire and inserted through the vascular cavity, and the implant is pushed or otherwise forced through the interior of the catheter to an aneurysm site.

Conventional implant delivery systems, however may exhibit a number of problems as a result of a gap between the guide wire and the outer sheath. First, while the guide wire may be able to turn and maneuver through curved vascular cavities or cavity divisions, such as a "Y" section or other division that splits a blood vessel, the outer sheath that follows the guide wire may not be able to complete these maneuvers. For example, if a blood vessel makes a sharp turn, the outer portions of the distal end of the sheath may abut against a vessel section or scrape against the inner vessel walls as the sheath attempts to follow the guide wire through sharp turns. As a result, the outer sheath can weaken or damage the blood vessel or release embolic debris or plaque further down the bloodstream. Second, the applications and treatments using conventional sheaths may be limited since it may not be possible to insert the sheath through narrow or curved vascular cavity sections to an aneurysm site. Consequently, the aneurysm or containment site can be left untreated or can be treated while causing damage to other blood vessel sections, in the process possibly leading to more serious injury, stroke and death. These problems are amplified with smaller vessels and vessels having sharp turns and when larger implants are utilized. Third, implants may not be properly retained within an aneurysm as a result of the width or the aneurysm neck. For example, an implant may be improperly secured or inadvertently released from the aneurysm as a result of slipping through a wide aneurysm neck.

A need, therefore, exists for a method and system that permits a delivery sheath and an implant, such as a vaso-occlusive implant or an embolic containment implant that facilitates delivery of a vaso-occlusive implant, to be maneuvered through various vascular spaces so that the implant is deployed at the proper location, such as an aneurysm, tumor, while reducing or minimizing damage to the vascular space and allowing implants to be secured or retained within the aneurysm.

SUMMARY OF THE INVENTION

In accordance with one aspect of the present invention is a method and system for delivering an implant, such as a vaso-occlusive implant, through a vascular space to a vascular site. A guide, a first member having a distal end and a proximal end and defining a first cavity, and a second member having a distal end and a proximal end and defining a second cavity are advanced along the guide and through the vascular space to the vascular site. The second member is inserted through the first member. When the members are positioned at the site, the second member and the guide are removed from the first cavity, and an implant is inserted through the first cavity and delivered to the vascular site with or without a guide wire.

The first member can be a first annular catheter defining the first cavity, and the second member can be a second annular catheter defining the second cavity. For example, the first annular catheter has an outer diameter of about 0.66 mm to about 1.3 mm, the first cavity has a diameter of about 0.5 mm to about 1.25 mm, the second annular catheter has an outer diameter of about 0.45 mm to about 1.20 mm, and the second cavity having a diameter of about 0.35 mm to about 1.0 mm.

With this configuration, the second member reduces radial movement of the first member relative to the guide, and the guide is confined to the second cavity when the first and second members are inserted through the vascular space. Further, the distal ends of the first and second members can be generally aligned when the are advanced along the guide.

In further accordance with the present invention is a method and system for delivering a first implant through a vascular space to a vascular site in a body. A first member has a distal end and a proximal end and defines a first cavity. A second member has a distal end and a proximal end and defines a second cavity. The second member is insertable within the first cavity. The distal ends of the first and second members are advanced along a guide and through the vascular space to the vascular site, thereby advancing the first implant to the vascular site.

The first implant can be advanced by the distal end of the first member, the distal end of the second member, or the distal ends of both members. Further, the distal ends of the first and second members can be generally aligned when they are advanced along the guide.

A second implant, such as a vaso-occlusive implant, can also be inserted through the second cavity of the second member into the vascular site. The second implant is contained within the vascular site by the first implant.

The second member reduces the radial movement of the first member relative to the guide, and the guide is confined to the second cavity when the first and second members are inserted through the vascular space.

The first member can be a first annular catheter defining the first cavity, and the second member can be a second annular catheter defining the second cavity. For example, the first annular catheter has an outer diameter of about 0.66 mm to about 1.3 mm, the first cavity has a diameter of about 0.5 mm to about 1.25 mm, the second annular catheter has an outer diameter of about 0.45 mm to about 1.20 mm, and the second cavity having a diameter of about 0.35 mm to about 1.0 mm.

BRIEF DESCRIPTION OF THE DRAWINGS

Referring now to the drawings in which like reference numbers represent corresponding parts throughout:

FIG. 1A is a front view and FIG. 1B is a partial cross-sectional view of a system having a cavity-reducing or lumen-reducing sheath according to the present invention;

DETAILED DESCRIPTION OF THE PREFERRED EMBODIMENTS

Figure 2A:
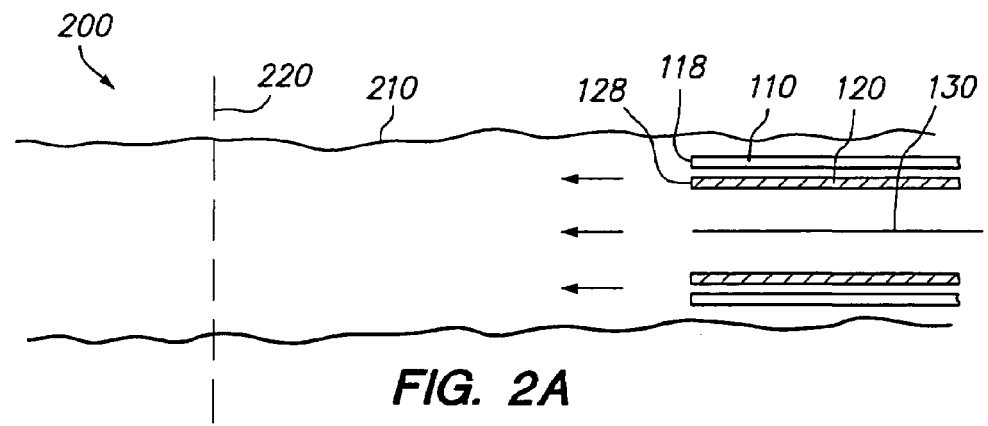
FIGS. 2A-J are partial cross-sectional views showing the manner in which an implant is inserted through a vascular space to a vascular site using an outer or delivery sheath, a lumen reducing sheath and guide wire.

Referring to FIGS. 1A-B, a system or assembly 100 of the present invention includes a first or delivery member 110, such as an outer, annular catheter or sheath, a second or reducing member 120, such as an inner, annular catheter or sheath, and a guide 130, such as a guide wire. The system 100 is used to deliver an implant (not shown) through a vascular space to a vascular site, such as an aneurysm, tumor, a site for capturing embolic debris, or other vascular malformation (generally vascular site).

The present invention is suitable for delivering or advancing various devices or implants into the body of a patient for different applications. For example, the present invention can be used to deliver a vaso-occlusive implant, such as a coil and a liquid, to treat or occlude an aneurysm. Further, the present invention can be used to deliver an embolic containment implant which facilitates delivery of a vaso-occlusive implant by, for example, reducing the size of the aperture formed by a neck of an aneurysm to contain the vaso-occlusive device in the aneurysm without risk of embolic migration. Typically, an embolic containment implant would be positioned slightly inside the neck of the aneurysm. Additionally, the present invention can be used to deliver a stent to ensure that a vessel remains open or unblocked. The stent can also be used to help contain subsequent delivery of embolic materials (liquids, coils) into the aneurysm, similar to an embolic containment implant. Unlike the embolic containment system, however, the stent is placed outside the neck of the aneurysm or into the parent vessel. An "implant" in this specification refers to the various types of implants that can be delivered with the present invention.

Persons of ordinary skill in the art will recognize that the implant can be delivered into the body through various entry points, e.g., percutaneously through a peripheral vessel, such as a femoral, carotid, or radial artery, or other vein, artery or vascular space, to treat various vascular sites. The present invention can be used to treat humans and animals. This specification, however, describes and illustrates a system and method related to treating a vascular cranial aneurysm sites with various implants for purposes of explanation and illustration, but the invention is not so limited.

Various guides 130 can be used with the system 100 of the present invention. One exemplary guide is a guide wire, such as a 1014 to GC18 guide wire, having diameters from about 0.01" to about 0.018". The guide wire can also have a rounded or modified tip, such as a "J hook" or a smoothed or rounded tip that allows the guide wire to be inserted through a vascular space more smoothly. Other exemplary guides include a guiding catheter or other guide rail. The particular guide 130 that is utilized may depend on the particular application. Thus, the invention is not limited to using a particular guide 130, but this specification refers to and illustrates a guide wire for purposes of explanation and illustration.

The outer, first or delivery catheter or sheath ("delivery catheter 110") may be a micro-catheter or other elongated delivery device. The size of the delivery catheter 110 can vary depending on the particular patient, treatment, and implant to be delivered to the aneurysm site. For example, when accessing a brain aneurysm in a small vessel, an appropriately sized delivery catheter 110 can be quite small and flexible.

Exemplary delivery catheters 110 for treating cranial aneurisms are 3.0 F to 3.8 F catheters having an outer diameter (OD) 112 from about 1.0 mm to about 1.3 mm. The inner diameter (ID) 114 of the lumen or cavity 116 of the delivery catheter 110 can be from about 0.8 mm to about 1.1 mm. Different delivery catheters 110 with different IDs 114 and ODs 112 can be utilized depending on the particular application and size of the implant. . The ID 114 of the delivery catheter 110, however, should be made large enough to accommodate a second or cavity-reducing or lumen-reducing catheter ("reducing catheter 120") and the implant.

The delivery catheter 110 can be made of different materials and have various coating to facilitate insertion through a vascular space. Exemplary delivery catheter 110 materials include Polypropylene, PE, Urethanes, Nylons, and Pebax. One exemplary coating applied to the outer surface of the delivery catheter 110 is a hydrophilic coating. Persons of ordinary skill in the art will recognize that various delivery catheter 110 sizes, materials, and coatings can be utilized depending on the particular application and treatment.

The second or reducing catheter 120 is inserted within the cavity or lumen 116 defined by the delivery catheter 110. The Outer Diameter (OD) 122 of the reducing catheter 120 should be smaller than the ID 114 of the delivery catheter 110 so that the reducing catheter 120 can be inserted through the lumen 116 of the delivery catheter 110. For example, if the delivery catheter 110 defines a lumen 116 with an ID 114 from about 0.5 mm to about 0.8 mm, then the OD 122 of the reducing catheter 120 can be from about 0.66 mm to about 1.0 mm. In one embodiment, the delivery catheter 110 defines a cavity having an ID 114 of about 0.033", and the reducing catheter 120 defines a reduced cavity or lumen 126 having an ID 124 from about 0.012" to about 0.021". As a result, with the reducing catheter 120, movement of the guide wire 130 is restricted to a smaller cavity or lumen compared to a larger lumen or cavity of a conventional delivery catheter. Similarly, with the reducing catheter 120, movement of the system 100 around the guide wire 130 is restricted to the smaller or lumen cavity 126, rather than a larger cavity of an outer catheter 110.

Thus, radial movement (e.g., up-down, side-to-side) of the assembly 110 including the delivery and reducing catheters 110 and 120 is limited compared to conventional systems, while allowing for the catheters to be inserted into a vascular space. With these exemplary configurations, the amount of movement or play between the guide wire 130 and the delivery catheter 110 is reduced so that the delivery catheter 110 can be inserted through a vascular space more easily and efficiently. For example, in one embodiment, the area of the first lumen 120 is reduced by about 35% to about 75%. Persons of ordinary skill in the art will recognize that different sizes and thickness of the catheters 110 and 120 can produce reduced cavities 126 of different sizes. Further, the gap between the catheters 110 and 120 can be adjusted as needed.

In use, the delivery and reducing catheters 110 and 120 are positioned in a vessel so that the distal ends 118 and 128 of the catheters 110 and 120 are advanced over or otherwise in conjunction with a guide wire 130 to a vascular site. For example, the distal ends 118 and 128 of the delivery and reducing catheters 110 and 120 may be generally aligned with each other when being advanced through the vascular space over the guide wire 130. The lumen-reducing catheter 120 can also extend somewhat ahead of the delivery catheter 110 if necessary.

If a vaso-occlusive implant is being delivered to an aneurysm site, the reducing catheter 120 and the guide wire 130 are removed after they are properly positioned at the vascular site. A displacement member, such as a pusher wire, advances the implant through the delivery catheter 110. Various other displacement members can be utilized, such as a plunger that is attached to the guide wire 130 to advance the implant or fluid pressure through the delivery catheter 110. When vaso-occlusive implants 230 are placed within or at a neck an of aneurysm 220, they tend to induce the formation of fibrin network (clot or thrombus). The thrombus provides a high-surface-area substrate on which the cells responsible for wound healing (such as fibroblasts) migrate and proliferate as they deposit collagen to replace the clot with more stable collagenous fibrous tissue.

In cases involving a first implant being delivered to an aneurysm site to retain or contain a second implant within an aneurysm site, the containment implant is inserted through a vessel together with the delivery and lumen-reducing catheters to a neck of the aneurysm. The containment implant reduces the width of a neck of an aneurysm. A second implant, such as a vaso-occlusive implant, is delivered through the reducing catheter to the aneurysm site and is secured or retained within the aneurysm by the previously deployed containment implant.

Having described components of a system 100 according to the present invention and the different manners in which they can be used, FIGS. 2A-I illustrate a method 200 and components of the system 100 at different stages showing in further detail how the system 100 is used to advance an implant, such as a stent, a coil, a filter or an implant that removes part of a vessel clot, to an aneurysm site.

Initially, referring to FIG. 2A, the guide wire 130 is inserted and fed through a vascular cavity or space 210. The delivery catheter 110 and the reducing catheter 120 are advanced over the guide wire 130. For example, as previously discussed, the delivery and lumen-reducing catheters 110 and 120 can be advanced together over the guide wire 130, and the catheters 110 and 120 can be generally aligned with each other as they are advanced over the guide wire 130. The reducing catheter 120 can also extend somewhat ahead of the delivery catheter if necessary.

Figure 2B:
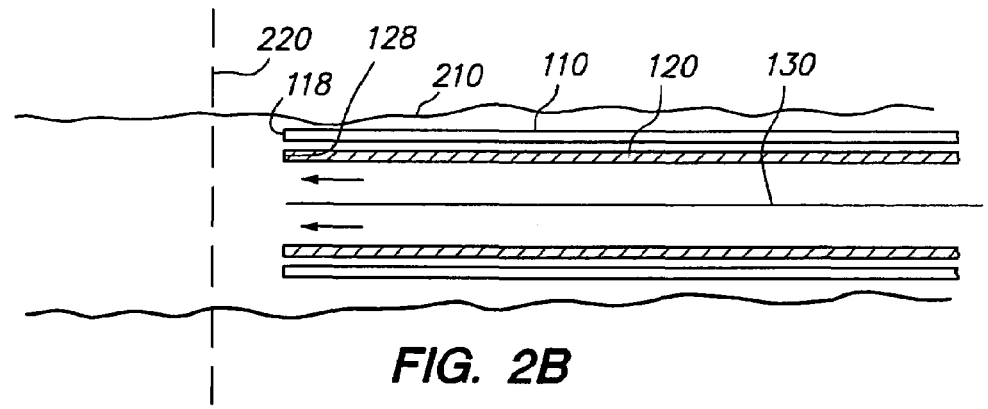
Figure 2C:
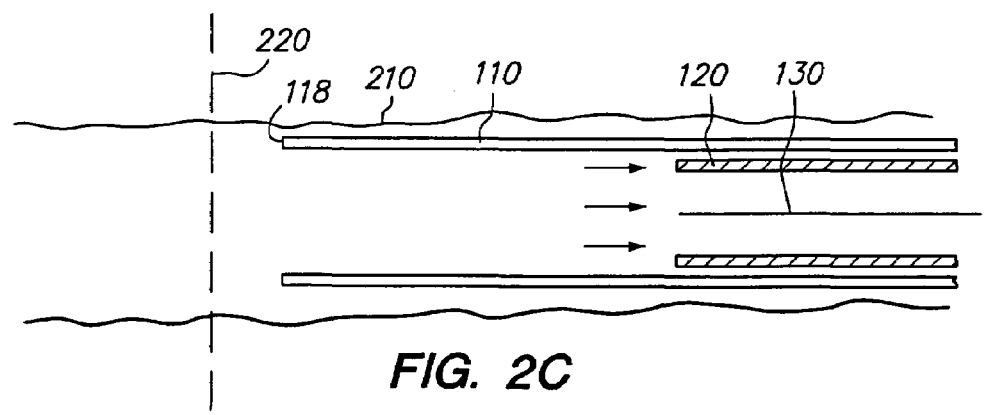
Figure 2D:
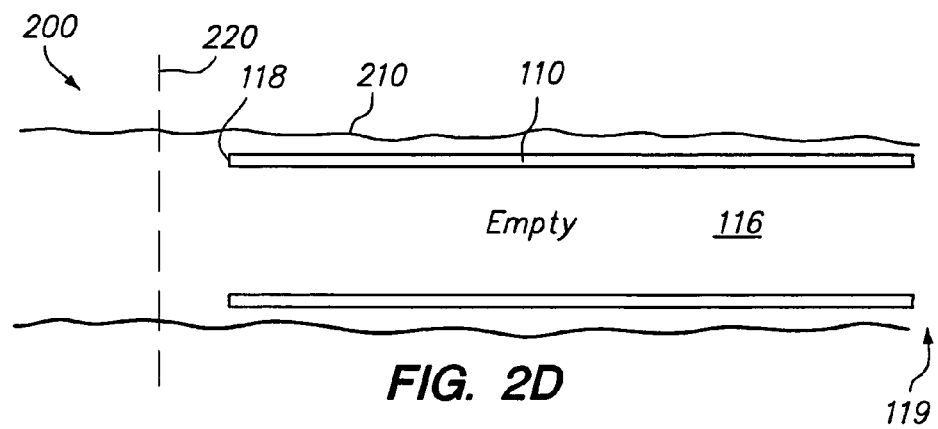

As the catheters 110 and 120 are advanced through the vascular space 210, as shown in FIG. 2B, the distal ends 118 and 128 of the delivery and reducing catheters 110 and 120 are positioned at or near the vascular site 220 (shown generally as a dotted line.) The site 220 is then said to be catheterized. Referring to FIG. 2C, the reducing catheter 120 and the guide wire 130 are retracted from the site 220 after the outer catheter 110 is positioned and, as shown in FIG. 2D, removed or pulled from the cavity 116 of the delivery catheter 110. As a result, only the delivery catheter 110 remains inserted within the vascular cavity 210 at the vascular site 220, and the lumen 116 of the delivery catheter 110 is empty.

Figure 2E:
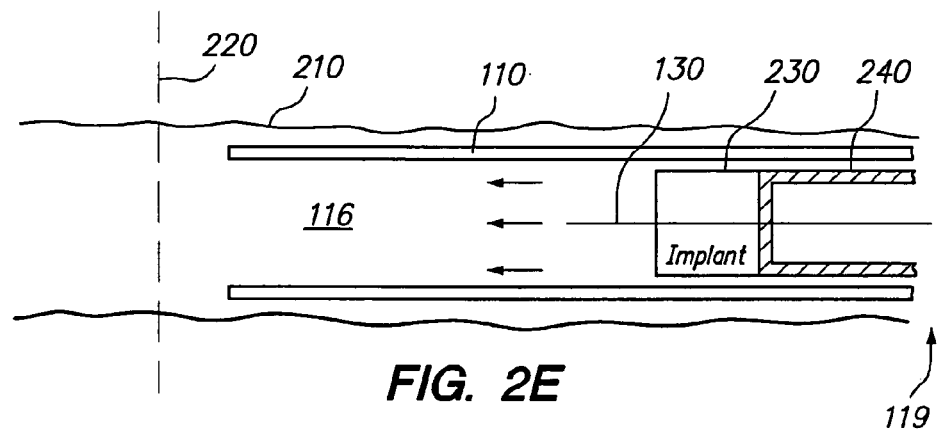
Figure 2F:
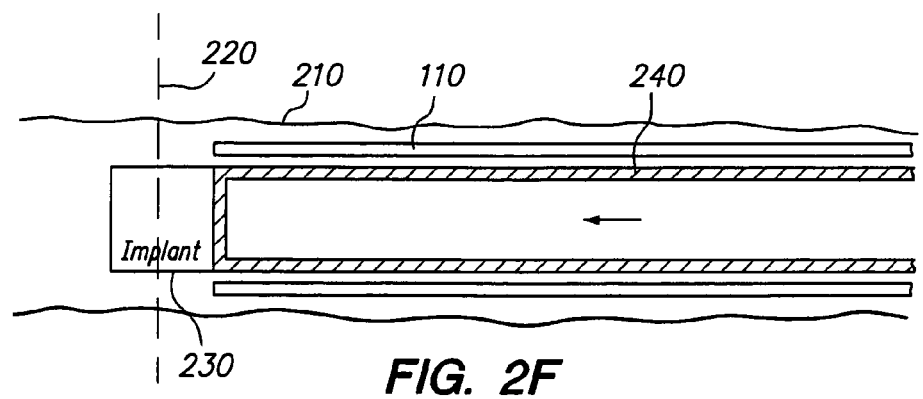

Referring to FIG. 2E, the guide wire 130 is re-inserted (or a different guide wire is inserted) into the lumen or cavity 116 of the delivery catheter 110. An implant 230, such as a vaso-occlusive coil, a stent, a filter, or an implant that removes part of a vessel clot is inserted into the proximate end 119 of the delivery catheter 110. An insertion or displacement device 240 advances the implant 230 along the guide wire 130 and through the cavity 116 of the delivery catheter 110 until the implant 230 exits or reaches the distal end 118 of the outer catheter 110, as shown in FIG. 2F. In an alternative embodiment, the implant 230 is pushed by the displacement device 240 through the cavity 116 of the delivery catheter 110 without a guide wire 130, however, a guide wire that directs the implant 230 to the site 220 is shown for purposes of illustration.

Figure 2G:
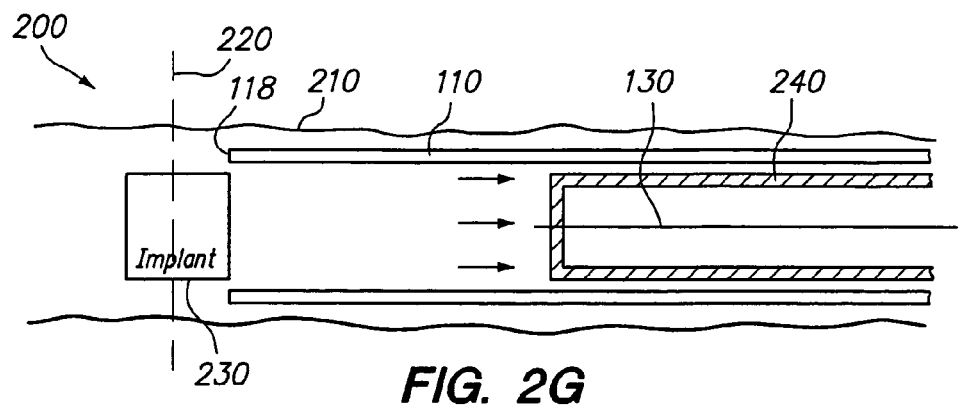
Figure 2H:
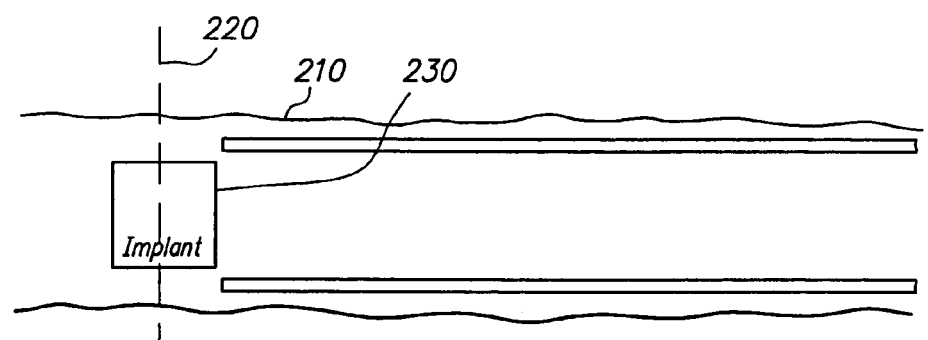
Figure 2I:
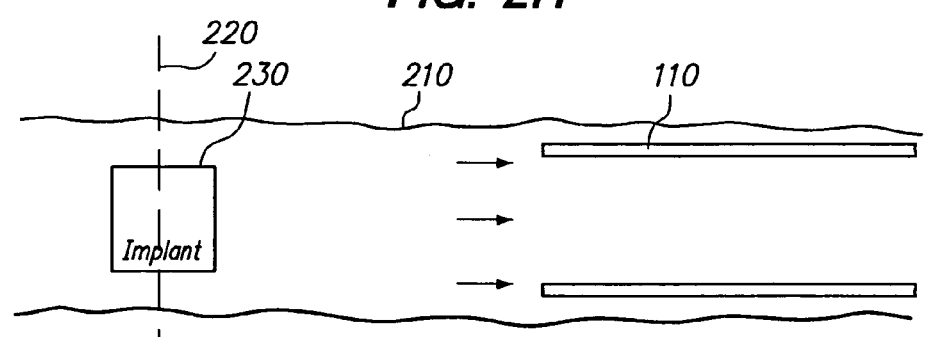
Figure 2J:
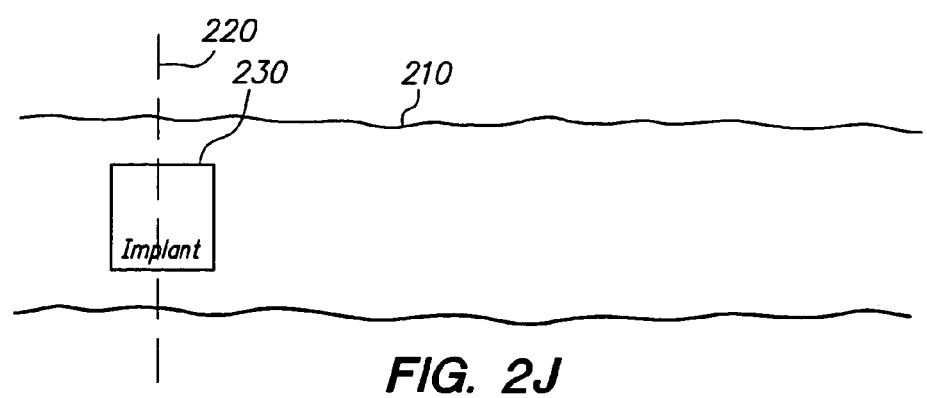

Referring to FIG. 2G, the displacement device 240 is detached or released from the implant 230 (if necessary), and the displacement device 240 and the guide wire 130 are removed from the lumen 116 of the delivery catheter 110. As a result, as shown in FIG. 2H, the implant 230 remains at the vascular site 220. As shown in FIG. 2I, the delivery catheter 110 may be removed from the vascular space 210, leaving the implant 230 at the site 220. The implant (e.g., a filter) may later be removed from the vascular space if necessary.

FIGS. 3A-F illustrate an alternative embodiment of the present invention directed to delivering an embolic containment implant and a second implant, such as a vaso-occlusive implant, utilizing a lumen-reducing catheter. For example, a containment implant can be delivered to the aneurysm neck to reduce the width of the neck, and a vaso-occlusive coil can then be delivered through the lumen reducing catheter into the aneurysm. As a result, the containment implant reduces the width of the neck to contain the coil within the aneurysm and retains the coil in the aneurysm while reducing the possibility that the coil will be inadvertently released from the aneurysm through the neck.

Figure 3A:
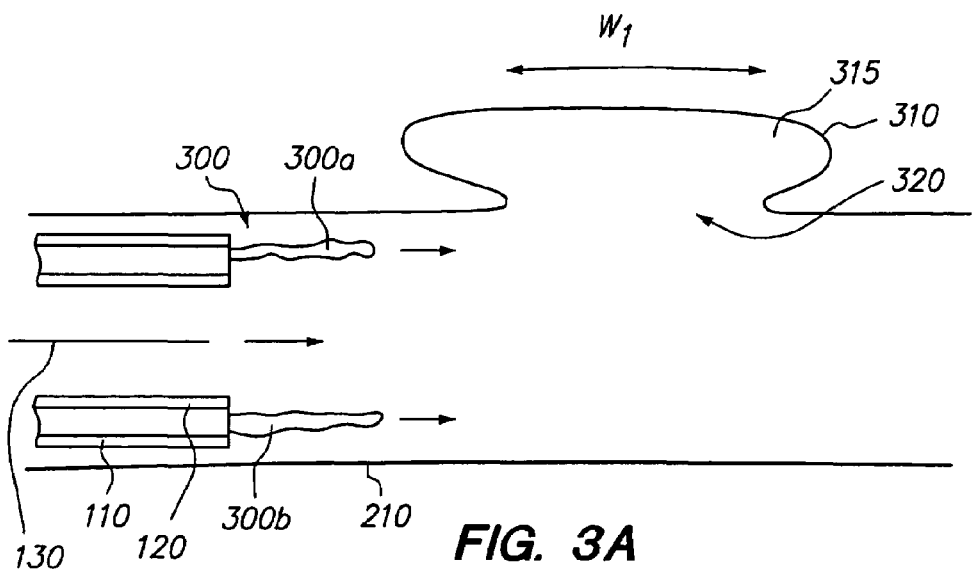
FIGS. 3A-F show how an embolic containment implant is delivered to a neck of an aneurysm and a second implant is then inserted into and retained within an aneurysm using a system and a method according to the present invention.
Figure 3B:
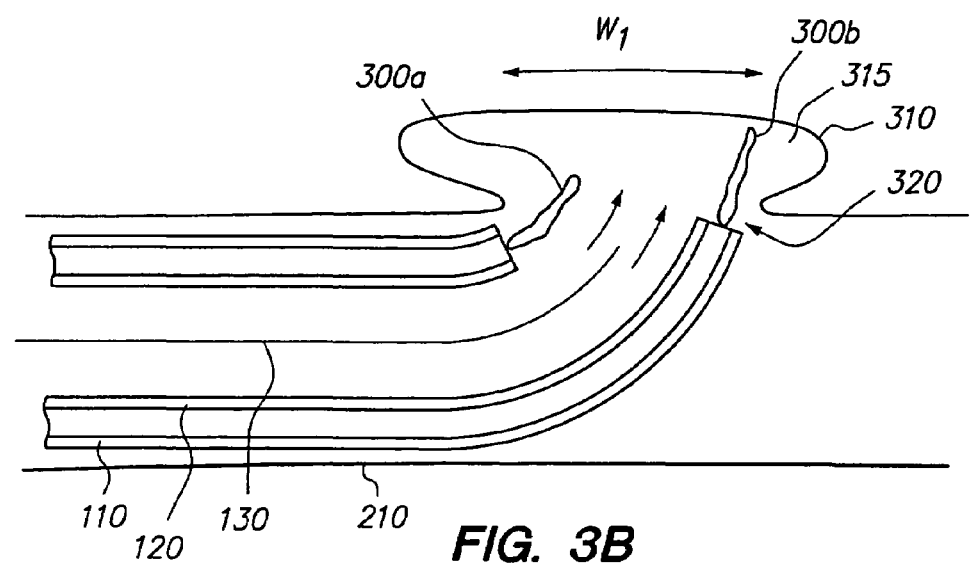
Figure 3C:
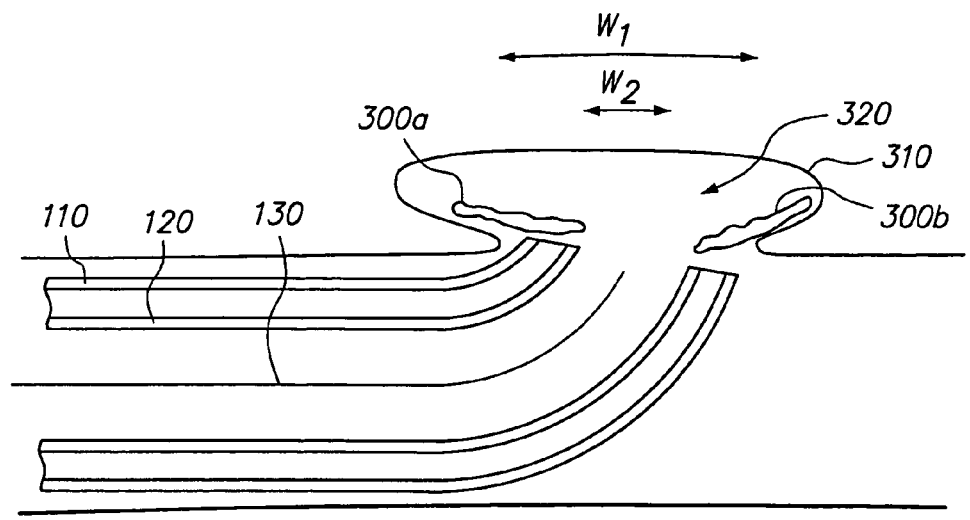

Specifically, referring to FIG. 3A, an embolic containment device 300, such as containment implants 300a and 300b (generally 300), are advanced together with the delivery and lumen-reducing catheters 110 and 120 and guided through a vessel 210 by a guide wire 130. As shown in FIG. 3A, an aneurysm 310 includes a sack or body 315 and a neck 320 with a width W1. Referring to FIG. 3B, the delivery system is advanced further through the vessel 210 so that the containment implants 300 are inserted into the aneurysm neck 320. As shown in FIG. 3C, the containment implants 300 are arranged so that they are placed within the aneurysm sack 315 and over part of the neck 320. As a result, the containment device 300 reduces the original width W1 of the neck 320 to a smaller width W2. The containment device 300 can expand to fill in the neck 320 and lower part of the aneurysm 310 in, for example, a disc-like shape or other shapes, depending on the site to be occluded.

Figure 3D:
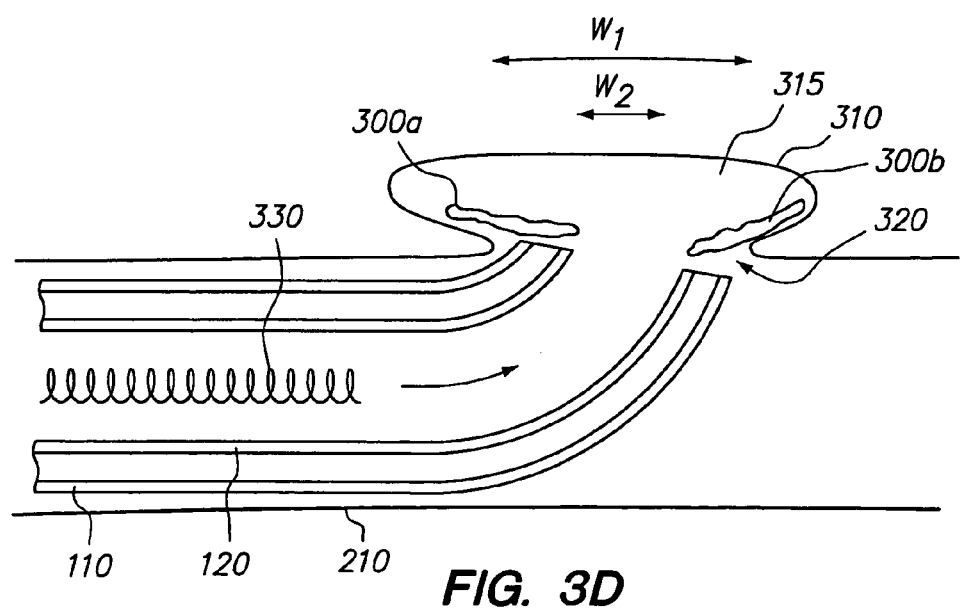
Figure 3E:
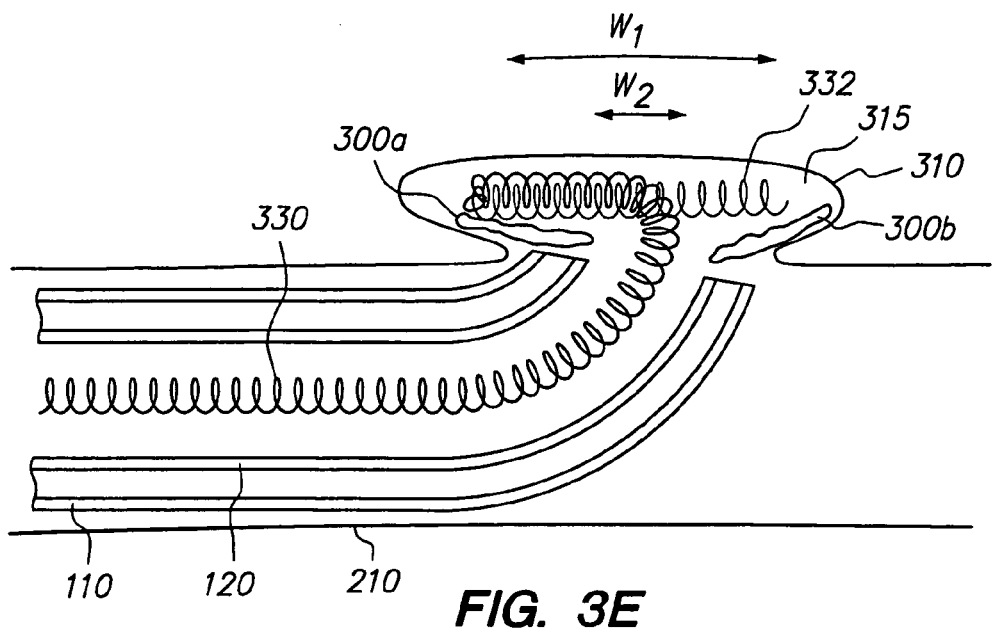
Figure 3F:
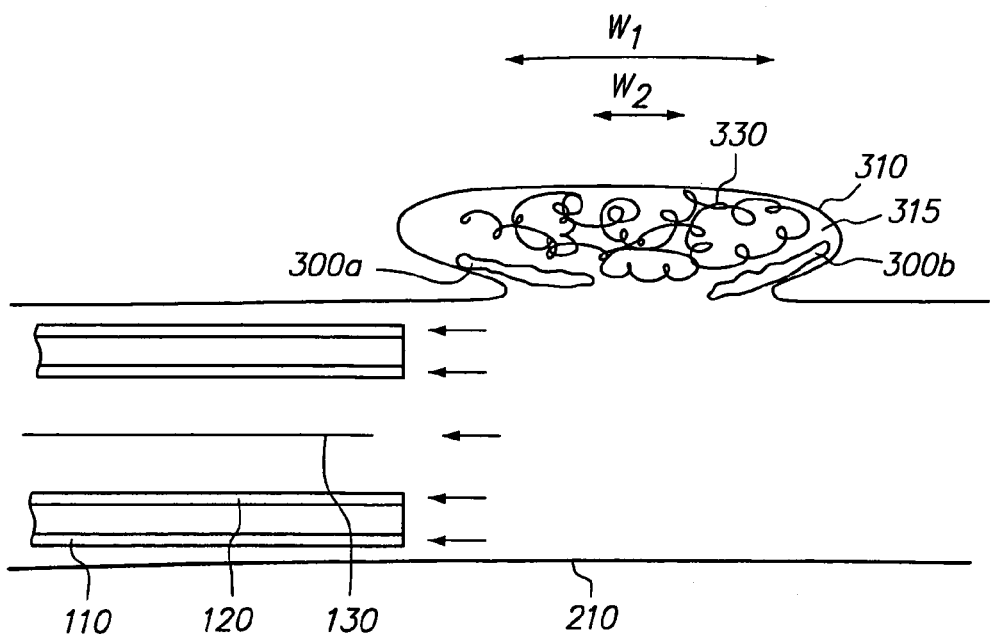

Referring to FIG. 3D, a vaso-occlusive device 330, such as a coil, is inserted through the lumen-reducing catheter 120 until, as shown in FIG. 3E, the distal end 332 of the coil 330 exits the distal end of the lumen reducing catheter 120 and is inserted into the sack 315 of the aneurysm 310 through or between the containment implants 300. In FIG. 3F, the coil 330 is inserted into the aneurysm sack 315 and retained by the containment implants 300. The delivery catheter 110, the lumen-reducing catheter 120, and the guide wire 130 can then be removed from the vessel 210, leaving the coil 330 and containment implants 300 behind at the aneurysm 310. The coil 330 can then assist in forming a thrombus to occlude the aneurysm 310.

Having described different systems 100 and a methods 200 according to the present invention, persons of ordinary skill in the art will appreciate that the present invention can be implemented with various types of guides 130, delivery catheters 110, reducing catheters 120, implants 230, and displacement or pusher members 240 to deliver the implants 230 through a vascular cavity 210 to a vascular site 220. The implant can be solely a vaso-occlusive implant, solely a containment implant that contains a vaso-occlusive implant, or serve as both a vaso-occlusive and a containment implant.

For example, one exemplary vaso-occlusive implant 230 is a vaso-occlusive coil that occludes the interior or sack of an aneurysm, such as a Guglielmi Electrolyctically Detachable Coil (GDC). A coil can assume a linear helical configuration when stretched and a folded convoluted configuration when relaxed. The coil has a stretched configuration when placed in the delivery catheter 110, which is used in placement of the coil at the desired aneurysm site , and assumes the convoluted configuration when the coil is ejected from the delivery catheter 110 and the coil relaxes. Other shapes, such as "flower" shapes, double vortices, and random shapes can also be used. Vaso-occlusive coils having more complex, three-dimensional structures in a relaxed configuration can also be utilized. The coils may be deployed in the approximate shape of a sphere, an ovoid, a clover, a box-like structure or other distorted spherical shape. Vaso-occlusive coils may also be made of various other biocompatible polymers or of carbon fibers. The vaso-occlusive implant may be covered or connected with fibrous materials tied to the outside of the coil or braided onto the outer cover of the coil as desired.

For occluding peripheral or neural sites, coils will typically be made of 1 mil to 5 mil diameter wire (e.g., platinum or platinum/tungsten alloy) that may be wound to have an inner diameter of 5 mils to 60 mils with a minimum pitch. The outer diameter is then typically between 0.007 and 0.700 inch. The length of the coil 230 will normally be in the range of 0.5 to 60 cm, preferably 0.5 to 40 cm. The coils may also be formed in such a way that they are essentially linear as they pass through the delivery catheter 110 and yet assume a randomly oriented relaxed condition after they are released from the end 118 of the delivery catheter 110.

A further exemplary implant 230 is a vaso-occlusive implant that includes an inner core wire covered with a polymer. The polymeric material includes protein based polymers, absorbable polymers, non-protein based polymers, and combinations thereof. The polymer facilitates forming of emboli to occlude a body cavity.

Other exemplary vaso-occlusive implants 230 include multiple vaso-occlusive members with electrolytically disintegratible links between the members. For example, a link may be relatively more susceptible to electrolysis in an ionic solution such as blood or most other bodily fluids than is a vaso-occlusive member. The link may also be tapered or otherwise modified, or coated with an insulative polymer and scored to limit the area of electrolytic disintegration of the link to a more discrete region or point.

The implant 230 can also have a fibrous structure carried by the core member. One exemplary fibrous structure includes one or more nano-scale fibers or nanofibers having diameters ranging from, for example, 50 to 10000 nm. The nanofibers may provide or enhance thrombogenic properties of the vaso-occlusive device. The core member is preferably made of a biodegradable material. Biodegradable or absorbable materials suitable for the core member may include, but are not limited to, synthetic polymers, polysaccharides, and proteins. Suitable polymers may include, for example, polyglycolic acid, polylactic acid, polycaprolactone, polyhydroxybutyrate, polyhydroxyvalerate, polydioxanone, polycarbonates, polyanhydrides, polyhydroxyalkanoates, polyarylates, polysaccharides, polyamino acids, and copolymers thereof. In addition or alternatively, proteins may be used, such as collagen, elastin, fibrin, fibrinogen, fibronectin, vitronectin, laminin, silk, and/or gelatin. In addition or alternatively, polysaccharides may be used, such as chitin, chitosan, cellulose, alginate, hyaluronic acid, and chondroitin sulfate. Many of these materials are commercially available. Fibrin-containing compositions are commercially available, for example from Baxter. Collagen-containing compositions are commercially available, for example, from Cohesion Technologies, Inc., of Palo Alto, Calif. Absorbable materials may be used alone or in any combination with each other. The absorbable material may also be a mono-filament or multi-filament strands.

The implant 230 can also be a device that disrupts an endothelium of a well of the aneurysm in this matter reduces the risk of the aneurysm wall expanding, thinning and/or rupturing.

As discussed in connection with FIGS. 3A-J, a further exemplary implant 230 is an embolic containment device. The embolic containment device is used to contain or secure a second implant, such as a vaso-occlusive implant, within an aneurysm by reducing the size of the aneurysm neck. One exemplary embolic containment device expands or opens in a "disc" like shape to fill the lower portion of the aneurysm sack, the neck of the aneurysm. The device can also extend down into the blood vessel to capture embolic debris. Exemplary embolic containment implant materials include, but are not limited to, braided polyester, nanofibers, and various mesh materials. In addition to containing a vaso-occlusive device within an aneurysm, the embolic containment device can also assist with healing the aneurysm since it serves as a scaffold across the aneurysm neck, thereby reducing blood flow and facilitating clotting.

A further exemplary implant 230 is a stent. A stent can serve as an embolic containment implant or a vaso-occlusive implant. For example, a stent can be used to reduce the size of the aneurysm neck, and a vaso-occlusive coil is inserted between stent sections into an aneurysm. A stent can also be covered or coated with materials that facilitate clotting so that the stent can be inserted into the aneurysm and occlude the aneurysm. For example, with reference to the embodiment shown in FIGS. 2A-J, a self-expanding stent can be attached to the distal end of the pusher member 240 as they are advanced through the outer catheter 110 and then be released upon reaching the aneurysm site.

One type of stent that can be delivered with the present invention is a self expanding stent, e.g., a NiTi self expanding stent. A balloon expandable stent, such as a polymer or stainless steel expandable stent, can also be utilized. Other exemplary stents include coated or non-coated stents, covered or partially covered stents, high density braid stents, and stents covered in-situ.

Other implants suitable for use with the present invention include blood filters and clot grabbers or implants that secure a segment of a clot in a vessel. These implants, however, may be removed from the vessel instead of being detached or released into an aneurysm or vascular site.

Further, persons of ordinary skill in the art will recognize that various implants 230 may be coated or mixed with radiopaque materials for fluoroscopy tracking through the vascular space 210. Exemplary radiopaque materials include, but are not limited to, metals (e.g. tantalum, gold, silver, tungsten, rhenium, palladium, rhodium, or platinum), barium sulfate, bismuth oxide, bismuth subcarbonate, and the like. One exemplary coating is a platinum/tungsten alloy, e.g., 8% tungsten and the remainder platinum. These metals have significant radiopacity and in their alloys may be tailored to accomplish an appropriate blend of flexibility and stiffness. They are also largely biocompatible. Certain polymers are also suitable as vaso-occlusive member material either alone or in conjunction with metallic markers to provide radiopacity. These materials are chosen so that the procedure of locating the vaso-occlusive member within the vessel may be viewed using radiography.

The particular type, design and configuration of an implant 230 that can be delivered with the lumen reducing catheter system 100 of the present invention can be selected based on various factors, such as the particular application, treatment, and patient.

The system and method of the present invention are advantageous compared to conventional systems since the present invention allows a delivery catheter to be inserted at a vascular site more effectively, while reducing or minimizing damage to surrounding vascular tissue and walls. The gap between the guide wire and the outer catheter is effectively minimized or reduced with the reducing catheter, allowing the distal ends of the delivery and reducing catheters to be maneuvered along the guide wire through sharper turns, "Y" sections and other divisions in blood vessels by limiting radial movement of the distal ends of the assembly. The delivery catheter is less likely to scrape against vessel walls or impact middle portions of "Y" sections or other divisions of vascular bodies, while following the guide wire through sharper turns, curves or blood vessel divisions compared to conventional systems.

Further, the present invention allows a vaso-occlusive implant, such as a coil, to be inserted within an aneurysm and to be retained in the aneurysm by a containment implant that effectively reduces the width of a neck of an aneurysm. As a result, the present invention reduces the likelihood that a coil will be improperly secured or inadvertently released from the aneurysm as a result of slipping through a wide aneurysm neck.

Various types and sizes of implants can then be inserted through the positioned outer or delivery catheter. Having described the improved method and system for delivering an implant according to the present invention, persons of ordinary skill in the art will recognize that the system and method can be modified in various ways to reduce the effective diameter or size of a delivery catheter lumen or cavity. For example, other delivery and reducing catheters with different sizes and proportions can be utilized. Further, various types and sizes of implants can be utilized including vaso-occlusive implants, such as a coil, an embolic containment device that facilitates delivery of a vaso-occlusive device, a stent and a filter.

Further, the present invention can be used to treat aneurysms, tumors or other vascular malformations. Although references have been made in the foregoing description to various embodiments, persons of ordinary skill in the art will recognize that insubstantial modifications, alterations, and substitutions can be made to the described embodiments without departing from the invention as recited in the accompanying claims.

What is claimed is:

1. A method of delivering a first implant and a second implant through a vascular space to a vascular site in a body, comprising:
    providing a guide, a first member having a distal end and a proximal end and defining a first cavity, and a second member having a distal end and a proximal end and defining a second cavity, the second member being insertable within the first cavity;
    advancing the distal ends of the first and second members along the guide and through the vascular space to the vascular site;
    removing the second member and the guide from the first cavity; and
    delivering the first and second implants through the first cavity and to the vascular site,
    before inserting the first implant, further comprising re-inserting the guide through the first cavity, the first implant being delivered along the guide and through the vascular space to the vascular site.

2. The method of claim 1, the second catheter reducing radial movement of the first catheter relative to the guide.

3. The method of claim 1, the guide being confined to the second cavity when the first and second catheters are inserted through the vascular space.

4. The method of claim 1, further comprising removing the first member from the vascular space.

5. The method of claim 1, advancing the distal ends of the first and second members further comprising advancing generally aligned distal ends of the first and second members along the guide and through the vascular space to the vascular site.

6. The method of claim 1, wherein the first member is a catheter defining the first cavity.

7. The method of claim 1, wherein the second member is a catheter defining the second cavity.

8. The method of claim 1, delivering the first implant further comprising delivering a vaso-occlusive implant.

9. A method of delivering a first implant and a second implant through a vascular space to a vascular site in a body, comprising:
    providing a guide, a first member having a distal end and a proximal end and defining a first cavity, and a second member having a distal end and a proximal end and defining a second cavity, the second member being insertable within the first cavity;
    providing a first implant and a second implant, each implant being configured for advancement through the vascular space using either of the first and second members;
    advancing the distal ends of the first and second members along the guide and through the vascular space to the vascular site, thereby delivering the first implant and the second implant to the vascular site, the first implant being advanced by the distal end of the first member.

10. The method of claim 9, the first implant being advanced by the distal ends of the first and second members.

11. The method of claim 9, further comprising removing the first member, the second member and the guide from the vascular space.

12. The method of claim 9, further comprising containing the second implant within a neck of the vascular site using the first implant.

13. The method of claim 9, advancing the second implant further comprising advancing a vaso-occlusive implant into the vascular site.

14. The method of claim 9, the vascular site comprising an aneurysm, the first implant being placed within a neck of the aneurysm.

15. The method of claim 9, the second member reducing radial movement of the first member relative to the guide.

16. The method of claim 9, the guide being confined to the second cavity when the first and second members are inserted through the vascular space.

17. The method of claim 9, advancing the distal ends of the first and second members further comprising advancing generally aligned distal ends of the first and second members along the guide and through the vascular space to the vascular site.

18. The method of claim 9, wherein the first member is a catheter defining the first cavity.

19. The method of claim 9, wherein the second member is a catheter defining the second cavity.

20. A method of delivering an implant through a vascular space to a vascular site in a body, comprising:

provides a guide wire, a first member having a distal end and a proximal end and defining a first cavity, and a second member having a distal end and a proximal end and defining a second cavity, the second member being insertable within the first cavity;

advancing the distal ends of the first and second members along the guide and through the vascular space to the vascular site;

removing the second member and the guide from the first cavity;

re-inserting the guide through the first cavity; and delivering the implant along the guide and through the first cavity and the vascular space to the vascular site.

21. A method of delivering an implant through a vascular space to a vascular site in a body, comprising:

providing a guide, a first member having a distal end and a proximal end and defining a first cavity, and a second member having a distal end and a proximal end and defining a second cavity, the second member being insertable within the first cavity; and advancing the distal ends of the first and second members along the guide and through the vascular space to the vascular site, thereby delivering the implant to the vascular site, the implant being advanced by the distal end of the first member.

* * * * *